(12) United States Patent
Schmidt et al.

(10) Patent No.: US 11,493,584 B2
(45) Date of Patent: Nov. 8, 2022

(54) METHOD AND APPARATUS FOR HYDROGENATION AND HYPERPOLARIZATION OF TRACER MOLECULES FOR MAGNETIC RESONANCE IMAGING

(71) Applicant: Albert-Ludwigs-Universitat Freiburg, Freiburg (DE)

(72) Inventors: Andreas Schmidt, Freiburg (DE); Jan-Bernd Hovener, Kiel (DE); Jurgen Hennig, Freiburg (DE); Stephan Berner, Freiburg (DE)

(73) Assignee: ALBERT-LUDWIGS-UNIVERSITAT FREIBURG, Freiburg (DE)

(*) Notice: Subject to any disclaimer, the term of this patent is extended or adjusted under 35 U.S.C. 154(b) by 0 days.

(21) Appl. No.: 17/266,009

(22) PCT Filed: Aug. 14, 2019

(86) PCT No.: PCT/EP2019/071777
§ 371 (c)(1),
(2) Date: Feb. 4, 2021

(87) PCT Pub. No.: WO2020/035518
PCT Pub. Date: Feb. 20, 2020

(65) Prior Publication Data
US 2021/0165062 A1  Jun. 3, 2021

(30) Foreign Application Priority Data
Aug. 14, 2018 (DE) .......... 102018119695.4

(51) Int. Cl.
*G01R 33/56* (2006.01)
*A61B 5/055* (2006.01)
*G01R 33/483* (2006.01)

(52) U.S. Cl.
CPC .......... *G01R 33/5601* (2013.01); *A61B 5/055* (2013.01); *G01R 33/483* (2013.01)

(58) Field of Classification Search
USPC .......................................................... 324/307
See application file for complete search history.

(56) References Cited

U.S. PATENT DOCUMENTS

| | | | |
|---|---|---|---|
| 2006/0127314 A1 | 6/2006 | Ardenkjaer-Larsen et al. | |
| 2009/0121712 A1* | 5/2009 | Han | A61P 43/00 324/307 |
| 2013/0150623 A1* | 6/2013 | Sajiki | C07B 35/02 564/421 |

FOREIGN PATENT DOCUMENTS

| | | |
|---|---|---|
| DE | 60313354 | 1/2008 |
| WO | 2010067076 | 6/2010 |

OTHER PUBLICATIONS

Google Translation of German Office Action for 10 2018 119 695.4 dated Aug. 8, 2019. (Year: 2019).*

(Continued)

*Primary Examiner* — Rodney E Fuller
(74) *Attorney, Agent, or Firm* — Volpe Koenig

(57) ABSTRACT

In a method (100 to 208) in which hyperpolarizable tracer molecules (20, 88 to 98) are hydrogenated and then optionally also hyperpolarized for magnetic resonance imaging, it is provided that, in a first method step (104, 202), a hydrogen solution (10, 12, 4) having a saturation factor of at least 50% be prepared and that the hydrogenation reaction (186 to 190, 206) not be triggered until a subsequent, second method step (106, 204). An apparatus (1) with which the method of the invention (100 to 208) is executable is also provided.

17 Claims, 6 Drawing Sheets

(56) References Cited

OTHER PUBLICATIONS

Google Translation of Written Opinion for PCT/EP2019/07171777, dated Aug. 14, 2018 (Year: 2018).*

International Society for Magnetic Resonance in Medicine, ISMRM, 2030 Addison Street, 7th Floor, Berkeley, CA 94704 USA, No. 163, Apr. 7, 2017 (Apr. 7, 2017).

Green R A et al. "The theory and practice of hyperpolarization in magnetic resonance using parahydrogen" Progress in Nuclear Magnetic Resonance Spectroscopy, Pergamon Press, Oxford, GB, vol. 67, 01, pp. 1-48, [retrieved on Mar. 15, 2012], Nov. 2012 (Nvo. 1, 2012).

Mewis, Ryan E. et al., "Probing Signal Amplification by Reversible Exchange using an NMR flow system" Magnetic Resonance in Chemistry, vol. 52, No. 7, 06, pp. 358-369, May 2014 (May 6, 2014).

\* cited by examiner

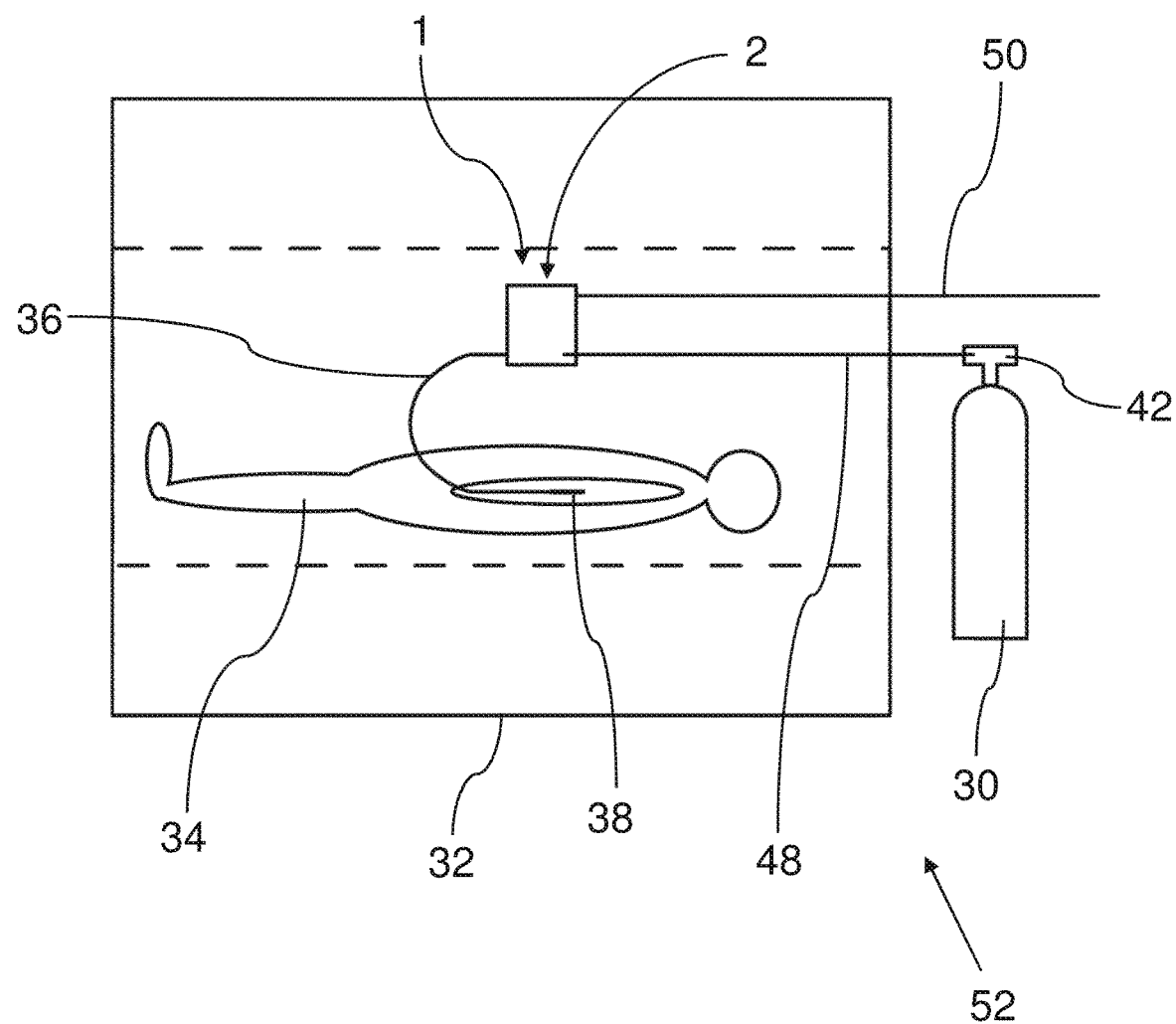

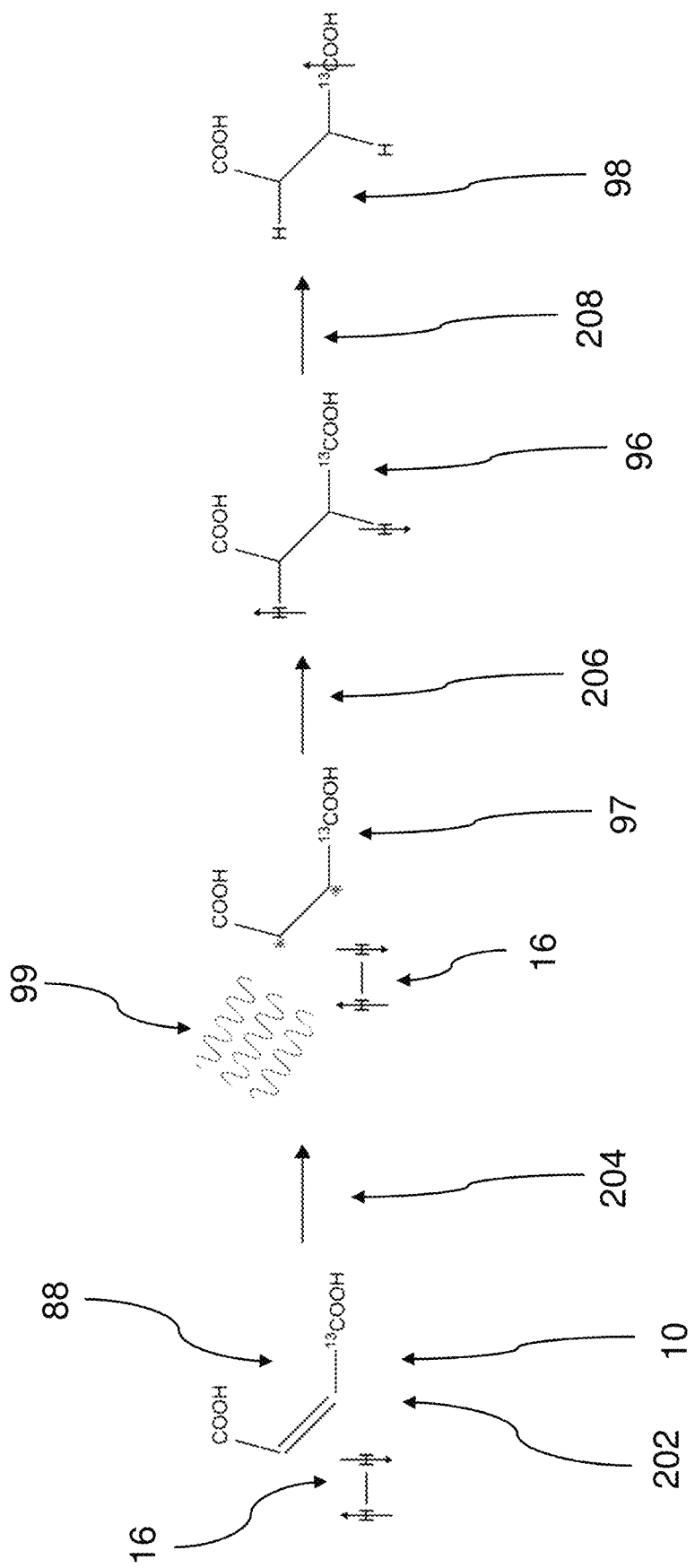

METHOD AND APPARATUS FOR HYDROGENATION AND HYPERPOLARIZATION OF TRACER MOLECULES FOR MAGNETIC RESONANCE IMAGING

TECHNICAL FIELD

The invention relates to a method in which hyperpolarizable tracer molecules are hydrogenated for magnetic resonance (MR) imaging, wherein the tracer molecules are brought into contact with hydrogen in a reaction mixture and a hydrogenation reaction is initiated in the reaction mixture.

The invention additionally relates to a method in which the tracer molecules hydrogenated by the method described above are hyperpolarized.

The invention further relates to a device for the hydrogenation of hyperpolarizable tracer molecules for MR imaging. The device has a reactor, this reactor including a first chamber having a first fill-volume, which has a feed line for hydrogen gas and/or for a liquid. For example, the first chamber may be an antechamber in which a hydrogen solution can be presaturated.

BACKGROUND

The hydrogenation of a tracer molecule can be characterized by the addition of hydrogen to an unsaturated compound of the tracer molecule.

The term "tracer molecule" is understood in a broad sense in the context of the invention. Tracer molecule is used in the context of this invention to refer not only to a hyperpolarized molecule, but also to such a molecule before hyperpolarization and also before hydrogenation. The application documents generally use the following specific expressions to describe the current state of the molecule: the tracer molecule in its ground state prior to hydrogenation is referred to as an "unsaturated tracer molecule" (such a molecule is also often referred to among specialists as a "precursor"), in its excited state as an "excited tracer molecule", after hydrogenation as a "hydrogenated tracer molecule", and after hyperpolarization as a "hyperpolarized tracer molecule".

The hyperpolarization of tracer molecules for MR imaging can be characterized in that, before performance of an MR measurement, the nuclear spins of the tracer molecules that are suitable or intended for the MR measurement are aligned to a degree far beyond thermal equilibrium. Thermal equilibrium may be exceeded by several orders of magnitude, for example by a factor of 10,000 or more. As a result of this, a measured MR signal of the hyperpolarized molecules can be enhanced by a corresponding factor.

Such methods and devices are known from routine practice.

An example of a known method for producing hyperpolarized tracer molecules is the method known as parahydrogen-induced polarization (PHIP).

It is known that hyperpolarized tracer molecules can be produced by initial enrichment with parahydrogen in a parahydrogen converter. In this process, hydrogen gas is passed into the converter. The hydrogen gas is then brought to thermal equilibrium at a low temperature of about 21 kelvin. Hydrogen is at room temperature in a para state to an extent of about 25% and in an ortho state to an extent of about 75%. At low temperatures, this equilibrium shifts in favor of the para state, with the result that, at 20 kelvin, most of the hydrogen molecules are in the para state. However, since quantum mechanics does not allow the transition from the ortho state to the para state, a catalyst such as iron oxide is used to accelerate the establishment of the thermal equilibrium in the parahydrogen converter. The parahydrogen thus enriched can then be stored for a period of two to three weeks, for example in a cylinder in fluid form, i.e. as a gas or—at higher pressure and/or at a lower temperature—as a liquid, before thermal equilibrium re-establishes itself at higher temperature. Storage can also be carried out at normal ambient temperatures, particularly in the gaseous phase of parahydrogen.

The storage time of parahydrogen is known to be reduced in solution. For example, the storage time in an organic solvent may be about two to three hours. Storage of parahydrogen for a normal period of time is therefore not possible in solution. The reason for the shortened storage time is that a return to the thermal equilibrium state occurs more quickly in solution.

Another known means of producing hyperpolarized tracer molecules is hydrogenation of the tracer molecules with enriched parahydrogen. In this method, the tracer molecules are brought into contact with hydrogen in a reactor and a hydrogenation reaction is initiated in the reactor. The hydrogenation reaction is usually accelerated catalytically. Various methods are known from the prior art.

In a first method, the tracer molecules are first mixed in dissolved form with a catalyst in the reactor. Parahydrogen gas is then passed into the reactor in a lower region. The bubbles evolved rise in the solution and, at the gas-liquid contact surfaces, the hydrogen gas passes into the solution. This gives rise to a reaction mixture. In the same method step, the hydrogenation reaction is initiated as soon as the hydrogen reaches a reaction center on a tracer molecule in the presence of the catalyst. The hydrogenation results in the uptake of hydrogen atoms by the tracer molecules.

In a second method, hydrogen gas is present in a reactor. A liquid in which the tracer molecules and the catalyst are mixed is then sprayed into the reactor. This results in gas-liquid contact surfaces forming at which hydrogen gas is taken up by the liquid. This results in the formation of a reaction mixture and the initiation of the hydrogenation reaction in the same method step as described above, as soon as hydrogen reaches the reaction centers of the tracer molecules.

A known means of producing hyperpolarized tracer molecules is to transfer the spin order of the hydrogen taken up by the tracer molecules to an MR-suitable atomic nucleus in the tracer molecule, for example a $^1H$, $^{13}C$, $^{15}N$ or $^{19}F$ nucleus, after or even during the hydrogenation. In this method, the hydrogenated molecules are subjected to a spin-order-transfer (SOT) sequence in a separate, low-field polarizer or directly in an MR scanner used for a subsequent measurement. The magnetic field variations generated by the SOT sequence manipulate the spins into states in which they enhance and selectively exchange spin order via the J couplings, resulting at the end of the SOT sequence for example in hyperpolarization of a particular $^{13}C$ nucleus or of another MR-suitable atomic nucleus in the molecules. For example, a 1-PH-INEPT+ sequence, a Goldman sequence or an ESOTHERIC sequence may be employed as the SOT sequence.

The hyperpolarization of a $^{13}C$ nucleus, especially before the hydrogenation is completed, can be advantageous, since the hyperpolarized state of a tracer molecule hyperpolarized in this way is longer-lasting and, in particular, is able to persist for longer than an ordered spin state of parahydrogen added to the tracer molecules. This methodology allows a hyperpolarized state in currently available tracer molecules to be maintained for some minutes, which can be sufficient for some medical applications.

It can therefore also be stated that, with the SOT sequence, spin order, which during the hydrogenation is introduced into the tracer molecules through the addition of an enriched isotope form of hydrogen such as parahydrogen, is transferred to an atomic nucleus in the tracer molecules that is suitable for the MR imaging or desired for a subsequent MR imaging, resulting in the alignment of the nuclear spin of such an atomic nucleus and thus in the hyperpolarization of the tracer molecule.

A medical application can consist for example in the injection of the solution containing hyperpolarized tracer molecules into a patient, using this solution as a contrast medium. The selected tracer molecule may for example be one that preferentially penetrates areas of tumor, with the result that the tumor tissue can show up more clearly than other tissues in a subsequent MR measurement. The preferential enrichment of tracer molecules in tumor tissue can also occur for example because perfusion may be increased as a result of increased energy demand in a tumor region. If using metabolically active tracer molecules, it is also possible for the tracer molecules to enter into a metabolic cycle. If this metabolic cycle has been pathologically altered as a result of a tumor, this can be detected by MR imaging, thereby allowing the tumor to be detected and, if necessary, characterized.

One disadvantage of the methods of the prior art is that the enrichment of parahydrogen in the reaction solution takes too long for many applications. This is because, after the addition of the hydrogen to the tracer molecules, a rapid decay of the ordered spin state means there are only a few seconds before transfer of the spin order to an MR-suitable atomic nucleus and subsequent addition of the tracer molecules to the measurement object and performance of the MR measurement.

This means that the hydrogenated solution of hyperpolarizable and/or hyperpolarized tracer molecules contains only a relatively low concentration of tracer molecules.

A further problem is the development of air inclusions formed through bubbling or spraying. These give rise to inhomogeneities in the magnetic field generated by the polarizer. What is problematic in particular is that inhomogeneities in the magnetic field result in shortening of the T2* relaxation times. This means that, even before the end of the application of a SOT sequence, a significant fraction of the hyperpolarized state of the tracer molecules will already have decayed and consequently no longer be available for subsequent imaging. Moreover, the inhomogeneities give rise to off-resonances, which means that, when a SOT sequence is employed, an optimal state in which the polarization could be transferred to, for example, the $^{13}$C nucleus does not arise.

A further problem with air inclusions is that air can also be injected during an intravenous injection, which can be very problematic for the patient's condition and in extreme cases could even lead to death.

The magnetic field inhomogeneities caused by air inclusions are particularly problematic in strong magnetic fields such as those used in imaging in humans or animals, for example in magnetic fields having a strength of 1.5 tesla, 3 tesla, 7 tesla or more. The prior art is therefore disadvantageous particularly when hyperpolarization is carried out not in a separate low-field polarizer, but directly in the MR scanner. The latter can be advantageous, since this eliminates the need for a separate polarizer and also reduces the time until administration of the tracer molecules for subsequent MR imaging.

From the publication "Long-lasting, liquid-state 13C hyperpolarization >20% generated in an MRI system within seconds enables fast 13C imaging", Proc. Intl. Soc. Mag. Reson. Med. 25 (2017), No. 0163, it is known to inject a hydrogenation by injecting parahydrogen from the bottom of a reactor used for the reaction.

From the publication Green et al. "The theory and practice of hyperpolarization in magnetic resonance using parahydrogen", PROGRESS IN NUCLEAR MAGNETIC RESONANCE SPECTROSCOPY, 67 (2012), pp. 1-48, DOI: 10.1016/J.PNMRS.2012.03.001, it is known to extend the contact time of parahydrogen in the solution by increasing the duration of bubbling into, or shaking of, the reaction mixture.

From the publication Mewis et al. "Probing signal amplification by reversible exchange using an NMR flow system", MAGNETIC RESONANCE IN CHEMISTRY, 52 (2014), pages 358-369, DOI: 10.1002/mrc.4073, it is known to bubble parahydrogen in the gaseous state into a reaction mixture.

What the methods described in the publications cited above have in common is that the hydrogenation action is already directly initiated by the preparation of the hydrogen solution.

SUMMARY

Against the background of what has been described above, the object of the present invention is to achieve more rapid hydrogenation of hyperpolarizable tracer molecules for MR imaging and/or to prevent air inclusions from forming in the hydrogenated solution. A further object of the present invention is to increase the concentration of the hydrogenated molecules in the hydrogenated solution.

To achieve this object, one or more features of the invention are provided. In particular, as a means of achieving the stated object, the invention thus provides a method in which the tracer molecules are hydrogenated for MR imaging.

The tracer molecules may be any molecules capable of being hydrogenated that can be used as tracers or contrast media for MR imaging. Examples of such molecules include 2-hydroxyethyl 1-$^{13}$C,2,3,3-D$_3$-acrylate (HEA) and its hydrogenation product 2-hydroxyethyl 1-$^{13}$C,2,3,3-D$_3$-propionate (HEP), or 1-$^{13}$C,2,3-D$_2$ fumarate and its hydrogenation product 1-$^{13}$C,2,3-D$_2$-succinate, or 2,2,3,3-tetrafluoropropyl 1-$^{13}$C,2,3,3-D$_3$ acrylate (TFPA) and its hydrogenation product 2,2,3,3-tetrafluoropropyl 1-$^{13}$C,2,3,3-D$_3$-propionate (TFPP), or vinyl acetate and its hydrogenation product ethyl acetate, or vinyl pyruvate and its hydrogenation product ethyl pyruvate. A particular advantage of this method is that the contrast medium solutions can be prepared without a potentially harmful catalyst.

The term "MR imaging" is understood in a broad sense in the context of this invention and encompasses not only tomographic MR methods but also spectroscopic MR methods of any kind. MR imaging is preferably imaging in a living being such as in a human or in an animal.

In the invention, the tracer molecules are brought into contact with hydrogen in a reaction mixture and a hydrogenation reaction is initiated in the reaction mixture. The initiation of the hydrogenation reaction results in the tracer molecules being hydrogenated. The hydrogenation reaction can also be characterized in that the hydrogen undergoes addition to the tracer molecules. For example, hydrogenation hydrogenates the unhydrogenated, unsaturated tracer molecule 2-hydroxyethyl 1-$^{13}$C,2,3,3-$D_3$-acrylate to the hydrogenated tracer molecule 2-hydroxyethyl 1-$^{13}$C,2,3,3-$D_3$-propionate. The reaction mixture can be characterized in that it is a homogeneous or heterogeneous mixture that contains all the substances involved in the hydrogenation reaction. The substances required for this purpose may all be dissolved in a liquid, they may be emulsified or they may also be in contact with one another in some other way, such as a solution in a reactor having an region on which one of the substances undergoing reaction is applied in solid form. For example, a catalyst may also be present in the reactor in solid form or mixed in heterogeneously. The term "emulsion" is understood in a broad sense in the context of this invention and, in addition to an emulsion in the true meaning of the word, also encompasses a suspension or a foam.

The reaction mixture typically consists of the tracer molecules, a catalyst, hydrogen, and a solvent such as water. As explained in more detail hereinbelow, the reaction mixture does not necessarily have to contain a catalyst. It may be that, in the reaction mixture, the tracer molecules and the catalyst form a complex having a reaction center. The complex may for example have a rhodium atom as the reaction center. The catalyst may contain the rhodium atom. For example, the catalyst may be prepared from a mixture of a bisphosphine ligand such as 1,4-bis [(phenyl-3-propanesulfonate)phosphine]butane disodium salt with a rhodium complex such as bis(norbornadiene)rhodium(I) tetrafluoroborate.

According to the invention, in a first method step the hydrogen is dissolved in a liquid, resulting in the preparation of a hydrogen solution having a saturation factor of at least 50%. The liquid may be water or another solvent suitable for dissolving hydrogen gas. The hydrogen is preferably dissolved in the liquid under elevated pressure.

The hydrogen to be dissolved is preferably provided in the form of hydrogen gas. This may be done, for example, as previously described above. The hydrogen gas provided may be enriched in one isotopic form. Deuterium and tritium are suitable as isotopes in addition to protium. These isotopes may be enriched, or become enriched, especially in their para form or in their ortho form. A particularly preferred isotopic form is parahydrogen of protium ($pH_2$).

The hydrogenation reaction is then initiated in a second method step following the first method step.

Presaturation of a hydrogen solution with hydrogen means that gas-liquid interfaces are avoided during the course of the hydrogenation reaction. On the one hand, this has the advantage of avoiding air inclusions having the disadvantages described hereinabove. In addition, this allows the hydrogen to reach the reaction centers of the tracer molecules very quickly, since the hydrogen is already present in dissolved form. Presaturation with a proportion of at least 50% also means that high concentrations of hydrogenated tracer molecules can be achieved in the reaction mixture within a very short space of time.

In order to further accelerate the enrichment of hydrogenated tracer molecules and to further increase the concentration of hydrogenated tracer molecules, it may be the case that the hydrogen saturation factor in the hydrogen solution is increased further. For example, it may be the case that the saturation factor is at least 80% or at least 85%. More preferably, the saturation factor is at least 90% or 95%. Particularly preferably, the saturation factor is at least 98% or 99%. A saturation factor of 100% can be very advantageous. In this case the hydrogen solution is completely saturated.

In a further embodiment of the method according to the invention, it may be the case that the reaction mixture is already prepared in the first method step. This may be done for example without a catalyst or with the use of a switchable catalyst. The switchable catalyst may for example be initially inactive and be activated only through the action of an activator such as light or sound. Alternatively or in addition, it may be the case that the hydrogenation reaction is initiated by activating a switchable catalyst, for example the switchable catalyst mentioned above, in the second method step. Such embodiments have the advantage that all the required substances can be mixed in a single vessel. This allows the hydrogenation reaction to take place with great rapidity, since the reactants can already be mixed with one another and the catalyst can be very swiftly activated, for example by exposure to light, i.e. by irradiating with light, which besides visible light can include ultraviolet (UV) light or infrared light, by irradiating with electromagnetic radiation of a different spectral range or by sonication.

In a further advantageous embodiment of the method according to the invention, it may be the case that the hydrogenation reaction is initiated by irradiating the reaction mixture in the second method step. Such an embodiment has the advantage that the hydrogenation reaction can proceed very swiftly and in a very controllable manner.

The irradiation may be effected by irradiating with electromagnetic radiation. The hydrogenation reaction may be initiated by activating a catalyst through irradiation. Alternatively, it is also possible for the hydrogenation reaction to be initiated without a catalyst as described below.

The electromagnetic radiation can preferably be visible light, ultraviolet light or infrared light. It can be particularly advantageous, in particular for initiating the hydrogenation reaction without a catalyst, if the UV light has a wavelength between 200 nm and 250 nm.

It is further preferable when the tracer molecules are brought to an excited electronic state by the irradiation. Particular preference is given to irradiating with electromagnetic radiation of a wavelength chosen such that the tracer molecule is brought to the excited electronic state by the irradiation. The chosen wavelength is particularly preferably one at which a photon has the energy needed for excitation of the electronic state. Excitation of the electronic state of the tracer molecule has the advantage of increasing the reactivity of the tracer molecule, with the result that the rate of reaction with the hydrogen present can increase. Because there is no need for a catalyst, such embodiments have the particular advantage that the hydrogenation reaction can be carried out very swiftly and in a particularly well controllable manner. In particular, this can be used to increase the proportion of hyperpolarized tracer molecules during spin-order transfer, thereby providing a stronger signal for a subsequent magnetic resonance measurement.

It is particularly preferable when the excitation of the electronic state brings the tracer molecules to a state in which a rate of incorporation of hydrogen into the tracer molecules is increased compared to tracer molecules in the unexcited state.

If the tracer molecule used is for example one having a carbon double bond, as is the case for example with an unsaturated fumarate, irradiation of the tracer molecule with UV light having a suitable wavelength of often between 200 nm and 250 nm will result in the tracer molecules being brought to an excited electronic state in which a carbon double bond is excited and therefore quasi-cleaved from a descriptive viewpoint. If the energy needed for excitation of the electronic state for the tracer molecule concerned is outside the corridor of 200 nm to 250 nm, the irradiation should preferably be effected with a corresponding light energy outside this wave range. The excitation of the carbon double bond makes the tracer molecules susceptible to the uptake of hydrogen. If hydrogen is present in the reaction mixture, the hydrogenation reaction is therefore initiated by the irradiation of the reaction mixture.

It is particularly preferable when the reaction mixture consists exclusively of a mixture of distilled water, hydrogen, and the tracer molecules. This can improve the efficiency of the hydrogenation, since the excited tracer molecules can find only hydrogen as reaction partner. A likewise preferred reaction mixture may also comprise further substances, the further substances being ones that do not react with the excited tracer molecules. The potential advantageousness of adding further substances, for example in order to increase the amount of hydrogenated substance, has previously been above described.

To accelerate the hydrogenation and to avoid air inclusions, it may alternatively be the case that the reaction mixture is not prepared until the second method step. It is preferable when the hydrogenation reaction is directly initiated by the preparation of the reaction mixture.

A particularly simple and quick method may be one in which the hydrogenation reaction is initiated by mixing the hydrogen solution with a further reactant or mixture of reactants in the second method step. The two constituents of the mixture produced that are to be mixed together may in particular be present here in separate vessels and mixed with one another by passing the contents of one vessel into the other vessel. The mixing can in particular be used to prepare the reaction mixture, as described above. It may be the case that the hydrogen solution is free of other reactants involved in the hydrogenation reaction, while the other mixture comprises the remaining reactants. It may also be the case that the hydrogen solution forms a mixture with at least one other substance involved in the hydrogenation reaction and that the other mixture comprises the other remaining reactants or just one of them. Thus, it is possible for example for the tracer molecules to be dissolved or emulsified in the hydrogen solution in the first method step and mixed with the catalyst in the second method step. It is likewise possible to mix the hydrogen solution with the catalyst in the first method step and with the tracer molecules in the second method step. The individual substances may be present dissolved, emulsified or in solid form.

To further increase the hydrogenation rate and/or the amount of hydrogenated substance, it may be the case that the liquid and/or the hydrogen solution and/or the reaction mixture is enriched with a substance that increases the uptake capacity of the liquid and/or of the hydrogen solution and/or of the reaction mixture for hydrogen. Addition of the substance preferably takes place before initiation of the hydrogenation reaction. The addition is particularly preferably carried out before or during a period of time during which the hydrogen is dissolved in the hydrogen solution. For example, the hydrogen solution may be admixed with, for example, ethanol and/or dimethyl sulfoxide, and/or the hydrogen solution can be Fluorinert or a Fluorinert mixture. For example, by admixing 10% ethanol with water, the amount of soluble hydrogen at 50 bar can be approximately doubled to about 80 mM.

The incorporation of hydrogen into the tracer molecules can be further improved when an H2 donor is added to the reaction mixture. Examples of suitable H2 donors are Cryptophan cages. The H2 donor may be added to the reaction mixture directly or this may take place indirectly, for example by first adding it to the hydrogen solution with which the reaction mixture is then prepared. The H2 donor is preferably removed again after the hydrogenation reaction. The H2 donor is preferably biocompatible.

The hydrogenation can be accelerated further when a further liquid in contact with a catalyst, for example the catalyst previously mentioned above, is presaturated with a hydrogen gas. This can for example bring about preactivation of the catalyst. It is preferable when the hydrogen gas presaturating the catalyst is normal hydrogen gas or parahydrogen gas. The catalyst may be dissolved or emulsified in the further liquid or else present in solid form. Such embodiments of the invention can be particularly advantageous in the case of catalysts that accelerate or initiate the hydrogenation reaction by means of heterogeneous catalysis.

To further accelerate the hydrogenation reaction and/or to increase the concentration of hyperpolarized tracer molecules, it may be the case that, in the first method step, the hydrogen gas is pressurized to above atmospheric pressure. For example, the pressure may be 50 bar. It is also preferable when the hydrogenation reaction is carried out under elevated pressure. Increasing the pressure can bring about an increase in the hydrogen saturation of the hydrogen solution and/or of the reaction mixture with hydrogen and/or with tracer molecules. At 50 bar, the concentration of dissolved hydrogen in water can for example be 40 mM. It is also possible for the hydrogenation reaction to be carried out at higher temperatures, since a boiling temperature can be increased. It is particularly preferable when the pressure at which the hydrogenation reaction is carried out is lower than the pressure present during dissolution of the hydrogen gas in the hydrogen solution. Such a pressure gradient can be advantageous in order to allow the reaction mixture to be prepared as effectively as possible.

It may be the case that the hydrogenation reaction taking place under elevated pressure is carried out below an actual boiling temperature and above a boiling temperature at atmospheric pressure. The boiling temperature relates here in particular to a liquid in which the hydrogenation reaction takes place, for example the previously mentioned liquid or further liquid. The hydrogenation reaction is preferably carried out above 100° C. It must be ensured that a catalyst is chosen that can withstand this temperature. Increasing the temperature has the advantage that the hydrogenation reaction is accelerated. As a result of the elevated pressure, the actual boiling temperature can rise beyond the atmospheric pressure boiling temperature, i.e. the boiling temperature at atmospheric pressure. The actual boiling temperature should generally not be exceeded, since this can otherwise result in the formation of large bubbles that can lead to air inclusions.

It may further be the case that, during or after initiation of the hydrogenation reaction, the pressure in a chamber of a reactor in which the hydrogenation reaction takes place, for example in the vessel previously mentioned above, is reduced, resulting in the escape of hydrogen as a consequence of supersaturation, with attendant bubble formation. Alternatively or in addition, the reduction in pressure may be effected such that a boiling point of a substance that is added to the reaction mixture and/or a boiling point of the reaction mixture is exceeded. Bubble formation could be advantageous, since the bubbles rising in the reaction mixture can form a hydrogen reservoir and can intensify the hydrogenation reaction. Evaporation can also be advantageous as a means of increasing the concentration of hydrogenated and/or hyperpolarized tracer molecules.

It may further be the case that, after initiation of the hydrogenation reaction, the reaction mixture is brought into contact with a hydrogen gas. It is preferable when this hydrogen gas is enriched in an isotopic form as previously described, for example in the form of parahydrogen gas. The above-described contacting can take place for example in combination with and/or using a method that is known per se, such as the bubbling method or spraying method previously described above. Combining these methods can result not only in the hydrogenation reaction proceeding with still greater rapidity, but in high concentrations of hydrogenated and/or hyperpolarized tracer molecules being at the same time producible.

It may further be the case that the hydrogenation reaction is carried out in a volume within a polarizer. The polarizer may be, for example, the variants of a polarizer described hereinbelow. It may also be the case that, during a period of time during which the hydrogenation reaction is taking place, spin order is transferred to an MR-suitable atomic nucleus in already-hydrogenated tracer molecules. The transfer of spin order may be carried out for example as set out elsewhere in this description.

To achieve the stated object, the invention provides the features of a method in which tracer molecules are hyperpolarized for magnetic resonance imaging. More particularly, to achieve the stated object the invention thus proposes for such a method that said method is executed using a method in which hyperpolarizable tracer molecules are hydrogenated for magnetic resonance imaging in a manner as described above.

The transfer of spin order to an MR-suitable atomic nucleus in the tracer molecules can be carried out according to methods known to those skilled in the art, for example by means of the spin-order-transfer sequence in a polarizer previously described above. The polarizer may be a low-field polarizer non-identical to the MR instrument with which the subsequent MR measurement of a measurement object is carried out. The polarizer may also be the MR instrument with which the MR measurement of a measurement object, especially of a study animal or patient, is to be carried out. The MR instrument may be a high-field polarizer in which a field strength of the main magnetic field is at least 1 tesla, at least 3 tesla or at least 7 tesla.

The transfer of spin order within the tracer molecules is carried out preferably within a period of time that begins as soon as, or after, the hydrogenation reaction is initiated. This period can therefore also begin after the hydrogenation reaction has ended.

To achieve the stated object, the invention provides the features of a device. More particularly, to achieve the stated object the invention thus proposes that, for a device of the type mentioned above, means are provided with which a method may be executed, in which hyperpolarizable tracer molecules are hydrogenated for magnetic resonance imaging, the method being in accordance with the invention, in particular as described above and/or as claimed in any of the claims directed to a corresponding method. The device is preferably configured for executing such a method of the invention.

In one embodiment of the device according to the invention, there may be a second chamber having a further fill-volume, the first chamber and the second chamber being connected to one another via a connecting line. In alternative embodiments it is also possible for further chambers to be provided.

The device may include a heating element, preferably for setting a temperature at which the hydrogenation reaction takes place, and/or means for setting a pressure in the first and/or in the second chamber. The means for setting a pressure may for example comprise one or more valves. The ability to set a temperature and/or defined pressures can be advantageous, as previously described above.

BRIEF DESCRIPTION OF THE DRAWINGS

The invention will now be described in more detail on the basis of some exemplary embodiments, but is not restricted to these exemplary embodiments. Further exemplary embodiments arise through combining the features of one or more claims with one another and/or with individual features as described above or with a plurality thereof.

FIG. 6 shows a measuring device prepared for an MR measurement in a patient, in which a device as shown in FIG. 4 or FIG. 5 is arranged.

FIG. 7 shows an alternative exemplary embodiment of a hydrogenation and hyperpolarization according to the invention of a tracer molecule for MR imaging by photochemical reaction and without the use of a catalyst.

DETAILED DESCRIPTION

In the following description of various exemplary embodiments of the invention, elements that correspond in their function are given corresponding reference numbers even if they are of different design or shape.

Figure 1:
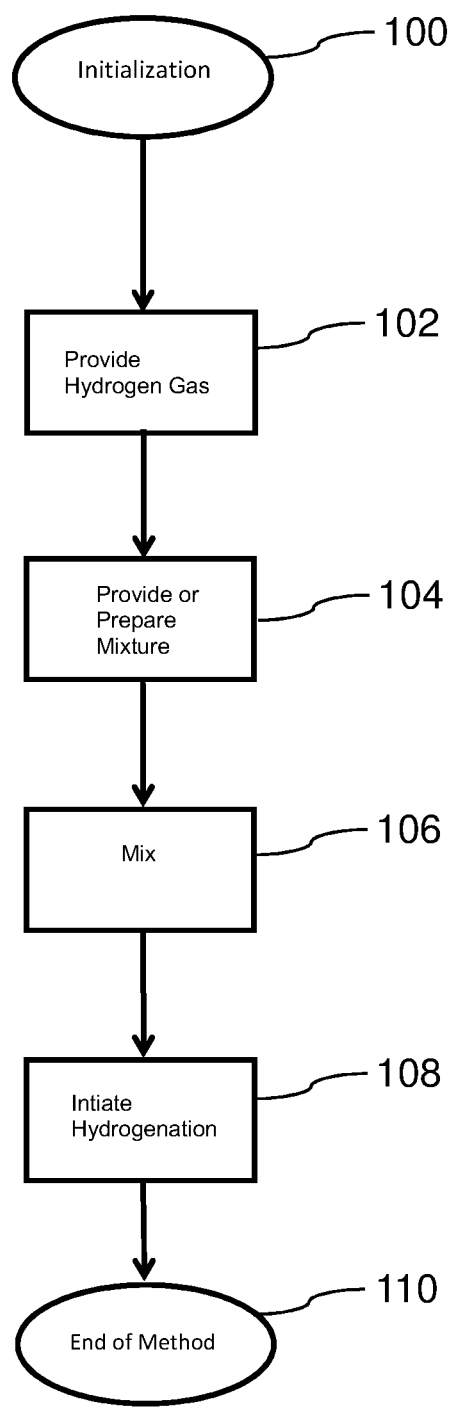
FIG. 1 shows a flow diagram of an exemplary embodiment of a method according to the invention in which hyperpolarizable tracer molecules are hydrogenated and hyperpolarized for MR imaging.

FIG. 1 shows a flow diagram of an exemplary embodiment of a method in which hyperpolarizable tracer molecules for MR imaging are hydrogenated and hyperpolarized in a manner in accordance with the invention.

The method is firstly initialized in step 100.

Figure 4:
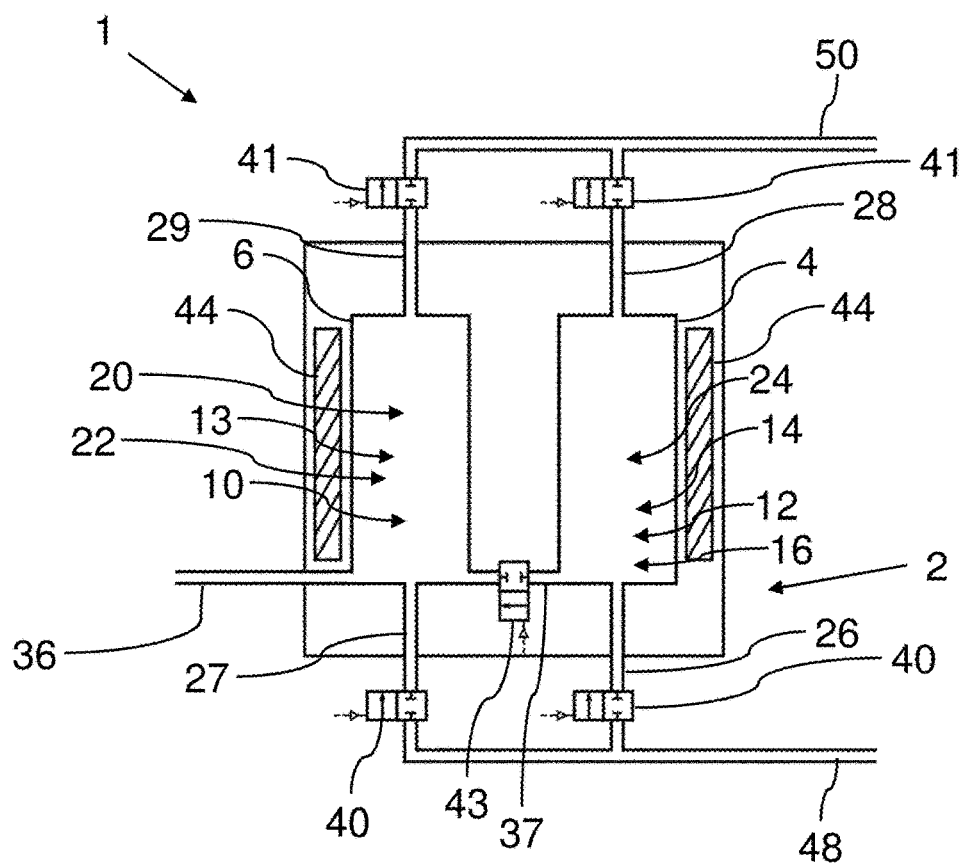
FIG. 4 shows an exemplary embodiment of a device according to the invention for the hydrogenation of hyperpolarizable tracer molecules for magnetic resonance imaging.
Figure 5:
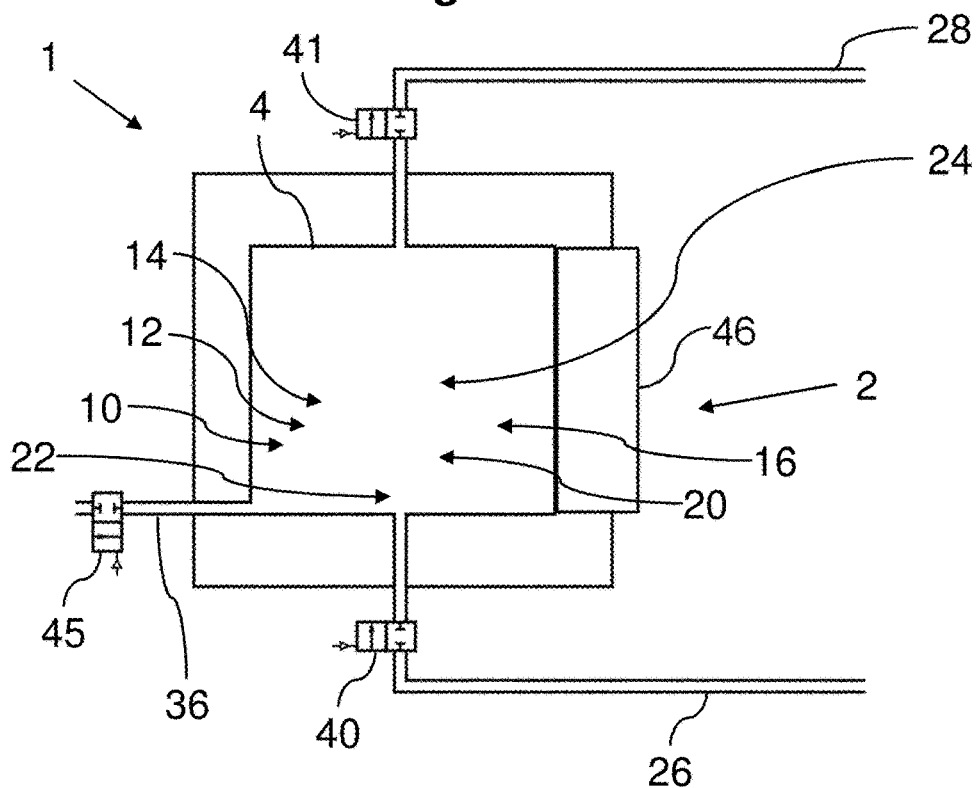
FIG. 5 shows an alternative embodiment of a device according to the invention for the hydrogenation of hyperpolarizable tracer molecules for magnetic resonance imaging.

In this step, the apparatus needed to execute the method is provided and set up. A possible embodiment of such an apparatus is shown in FIGS. 4 to 6 and is described in more detail hereinbelow. When setting up the apparatus in the exemplary embodiment described here, a cylinder 30 filled with parahydrogen is connected to a reactor 2. In addition, sources are connected to the reactor 2, which provide the other substances needed for execution of the method, such as in particular the catalyst 22, 86 and the still-unsaturated tracer molecules 20, 88. If an MR measurement of a patient 34 is to follow after completion of the method, a patient 34 can be positioned in an MR scanner 32, a cannula 38 can be fitted, and the cannula 38 can be connected to an outlet line 36 from the reactor 2. During initialization of the method, initial positions of valves 40, 41, 43, 45 are additionally set in the exemplary embodiment described here.

After initialization of the method, hydrogen gas 18 is provided in the form of parahydrogen gas in step 102. This can be done, for example, by opening a valve 42 on the cylinder 30 filled with parahydrogen gas. Alternatively, it may for example also be the case that the parahydrogen gas is provided by first generating the parahydrogen in a parahydrogen converter, for example as previously described above.

In a next step 104, mixtures of substances needed later for the hydrogenation reaction are then provided and/or prepared. As described in the exemplary embodiment, a hydrogen solution 14 is first prepared in a first chamber 4 of the reactor 2 by passing the parahydrogen gas provided in step 102 into the first chamber 4, wherein water is present in the first chamber 4. For example, this can be done by bubbling parahydrogen gas into the water for 5 minutes. In an alternative embodiment, a different solvent is present in chamber 4, which is provided with 10% ethanol. In addition, in step 104 a further mixture of substances is prepared in a second chamber 6 of the reactor 2 by passing into chamber 6 the hyperpolarizable tracer molecules 20, 88 for the MR imaging and the catalyst 22 already dissolved or emulsified in water or by adding these substances to a further liquid 13 present in chamber 6, which may be water. In an alternative embodiment, the tracer molecules 20, 88 are mixed with the hydrogen solution 14 in chamber 4 before this mixture is passed into chamber 6 for hydrogenation.

In step 106, the substance mixtures provided and/or prepared in step 104 are then mixed with one another. This is done by opening a valve 43 on a connecting line 37 between chambers 4 and 6. Since the first chamber 4 is pressurized to a higher pressure than the second chamber 6, this results in the hydrogen solution 14 flowing from the first chamber 4 into the second chamber 6 via the connecting line 37 connecting the first chamber 4 with the second chamber 6. As a result of the mixing of the substance mixtures, the hydrogenation reaction is initiated and the tracer molecules 20 are hydrogenated.

Initiation of the hydrogenation reaction is followed in step 108 by the transfer of spin order from the hydrogen atoms added to the tracer molecules 20 to an MR-suitable atomic nucleus in the tracer molecules 20. The polarizer configured as an MR scanner 32 is controlled with an SOT sequence for this purpose. The hyperpolarized tracer molecules 20 thereby prepared are then ready for further use in outlet line 36 from the reactor 2.

The method is then completed in step 110. This can be followed by an MR measurement carried out by means of MR scanner 32. This is done by opening a valve 45 shutting off line 36, which results in passage of the hyperpolarized tracer molecules 20 into the bloodstream of the patient 34 via the cannula 38, allowing the tracer molecules 20 to be used as contrast media for the subsequent MR measurement.

Figure 2:
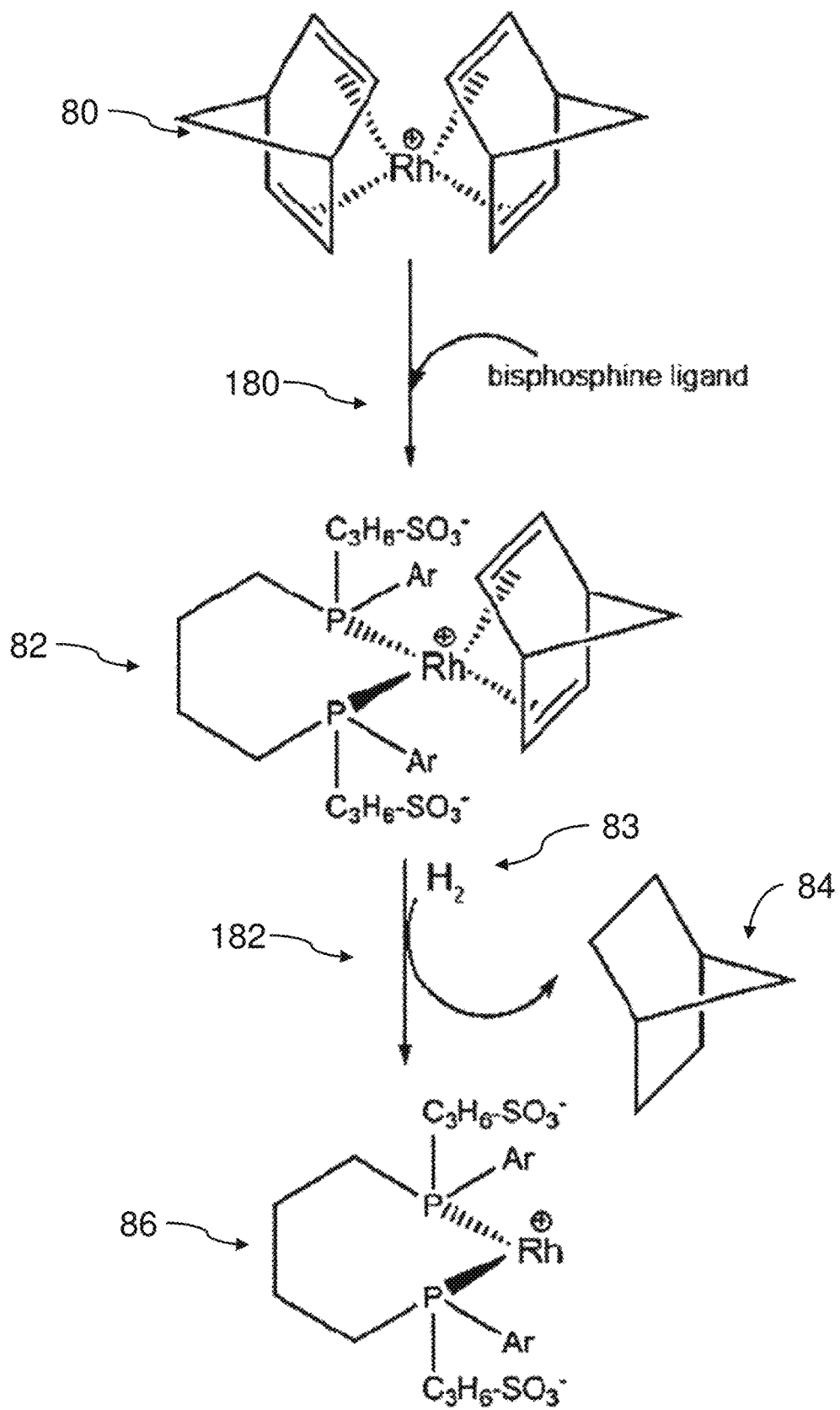
FIG. 2 shows an exemplary embodiment of a preparation of a catalyst that can be used for executing the method shown in FIG. 1.

FIG. 2 shows an exemplary embodiment of a preparation of a catalyst 22, 86 that can be used for executing the method shown in FIG. 1.

The starting point is a complex 80, which consists of two norbornadiene and a central rhodium atom. This complex 80 is first dissolved, for example in acetone or in warm water. A bisphosphine ligand is then added to the solution in step 180. This initiates an exchange reaction 180 in which one of the two norbornadiene is exchanged for the bisphosphine. This results in the formation of a complex 82 that consists of a norbornadiene molecule, a bisphosphine ligand and a central rhodium atom. Then, in step 182, the remaining norbornadiene molecule 84 is cleaved from the complex 82 by adding normal hydrogen gas 83, thereby generating the catalyst 86 for further use. For example, it is possible for a catalyst solution having a catalyst concentration of 20 mM to be thus produced.

Figure 3:
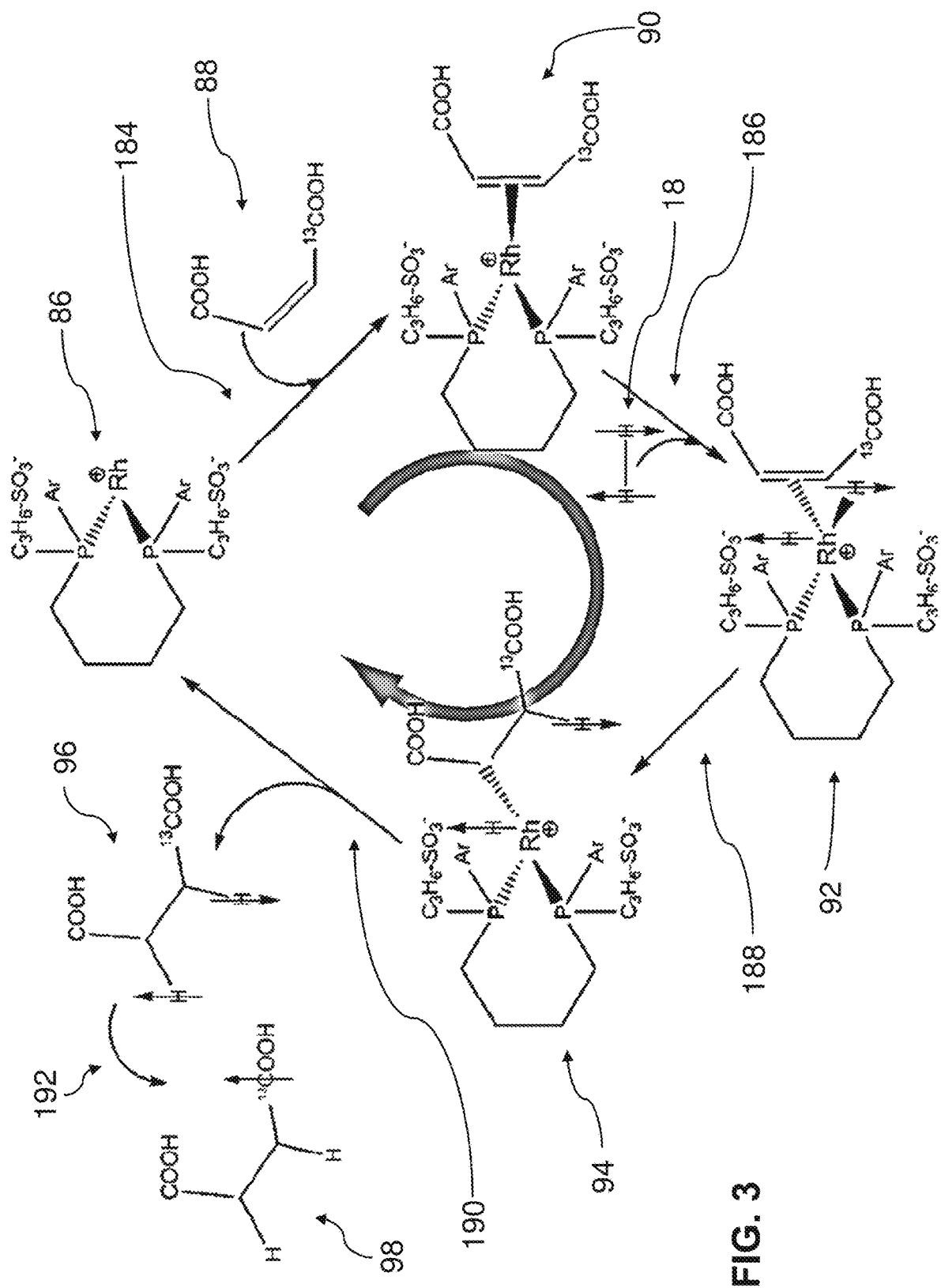
FIG. 3 shows an exemplary embodiment of a hydrogenation and hyperpolarization according to the invention of a tracer molecule for MR imaging, this being done using the catalyst shown in FIG. 2.

FIG. 3 shows a hydrogenation and hyperpolarization according to the invention of a hyperpolarizable tracer molecule 20, 88 to 98 for MR imaging, this being done using the catalyst 22, 86 shown in FIG. 2.

For this purpose, unsaturated tracer molecules 88, which in the exemplary embodiment described here constitute a fumarate containing a $^{13}C$ nucleus, are in step 184 first added to the prepared catalyst solution containing the catalyst 86. This generates a complex 90 made up of the catalyst 86, the unsaturated tracer molecule 88, and a central rhodium atom. The solution may, for example, contain tracer molecules 20, 88 in a concentration of 50 mM.

In a subsequent step, which corresponds to the previously described step 106, a hydrogen solution 14 containing dissolved hydrogen gas 18 present in the form of parahydrogen gas is in step 186 added to the solution containing the complex 90. This results in the initial formation of a complex 92 made up of the unsaturated tracer molecule 88, the catalyst 86, and a central rhodium atom with added parahydrogen. This is then followed by the actual hydrogenation reaction 188, in which the parahydrogen atoms migrate from and/or via the rhodium atom to the tracer molecule 20, 88, 96. This results in the formation of a complex 94 made up of the hydrogenated tracer molecule 96, the catalyst 86, and a central rhodium atom. Then, in step 190, the hydrogenated tracer molecule 96 cleaves from the catalyst 86. This completes the hydrogenation of the tracer molecule 20, 88 to 98.

In a subsequent step 192, which corresponds to the previously described step 108, the tracer molecule 20, 96, 98 is then hyperpolarized through transfer of spin order to the $^{13}C$ nucleus, resulting in the generation at the end of this process of a hyperpolarized tracer molecule 98.

The processes shown in FIGS. 2 and 3 merely depict a specific example. It is also possible to use/employ other types of catalyst 22, tracer molecule 20, and variations in the process sequence.

An advantageous variant of the method in which there is no need for a catalyst 86 is shown in FIG. 7. In a first step 202, a reaction mixture 10 that comprises hydrogen 16 and unsaturated tracer molecules 88 is first prepared.

The reaction mixture can be prepared in particular using the hydrogenation device 1 shown in FIG. 5 and described in more detail hereinbelow, but also using the device 1 illustrated in FIG. 4. The device 1 shown in FIG. 5 has only has a single chamber 4 into which a solution is introduced in which the unsaturated tracer molecules 88 and the hydrogen 16 are dissolved and/or emulsified.

The hydrogen 16 can be added to the solution for example by bubbling in a hydrogen gas 18 or else dissolved beforehand in a separate liquid that is then added to the chamber 4. This could also be done using a device 1 having two chambers 4 as shown for example in FIG. 4.

The order in which the preferably dissolved or emulsified unsaturated tracer molecules 88 are introduced and the hydrogen 16 is introduced can vary according to the embodiment of the method.

Preparatory steps may be carried out as previously described above, for example the above-described provision of the hydrogen gas in the form of parahydrogen gas.

After preparation of the reaction mixture in step 202 having at least 50% hydrogen presaturation, the reaction mixture 18 is then irradiated with electromagnetic radiation in a subsequent step 204 without further addition of hydrogen gas 18 or with further addition of hydrogen gas 18, resulting in the unsaturated tracer molecules 88 being brought to an excited electronic state, thereby forming excited tracer molecules 97. Depending on the embodiment of the tracer molecules 88, this can be done using for example UV light having a wavelength between 200 nm and 250 nm. For example, by irradiating tracer molecules 88 having a carbon double bond, such as in the case of a fumarate, the carbon double bond can be brought to an excited state.

As a result of this excitation, tracer molecules 97 thus excited become highly reactive and look for a reaction partner. Since hydrogen 16 is present in the reaction mixture 10, the hydrogen 16 is taken up by the excited tracer molecules 97, resulting in the initiation of a hydrogenation reaction 206. In FIG. 7, the excited electrons are depicted by an asterisk. In the specific embodiment shown in FIG. 7, electrons of the carbon atoms involved in the carbon double bond are excited. The invention also encompasses other excited states of the tracer molecules 88, 97 used in each case.

The hydrogenation results in the formation of hydrogenated tracer molecules 96.

As previously described above, the hydrogenated tracer molecules 96 can then undergo hyperpolarization in step 208 by means of a transfer of spin order to a 13C nucleus in the hydrogenated tracer molecule 96.

FIG. 4 shows an exemplary embodiment of a device according to the invention for the hydrogenation of hyperpolarizable tracer molecules 20, 88 to 98 for MR imaging.

The device 1 comprises a reactor 2 having a first chamber 4 and a second chamber 6. The reactor 2 has an inlet 48 which divides into a feed line 26 of the first chamber 4 and a feed line 7 of the second chamber 6. On the outlet side, the reactor 2 has an outlet 50 on an upper side at which an outlet 28 from the first chamber 4 and an outlet 29 from the second chamber 6 merge. In the lower region of the second chamber 6, said chamber additionally has an outlet line 36 on the outlet side. This line 36 can be connected for example to an injection catheter. The reactor 2 also has heating elements 44 with which a first temperature in the first chamber 4 and a second temperature in the second chamber 6 can be set. For example, the first temperature can be 75° C. and the second temperature 60° C. In addition, the valves 41 on the outlets 28, 29 provide the reactor 2 with a means of setting a first pressure in the first chamber 4 and a second pressure in the second chamber 6, the pressures in each case being limited by the pressure set on the inlet side at inlet 48.

Controllable valves 40, 41, 43, 45 are positioned at the connections of the first chamber 4 and second chamber 6. The valves 40 in the feed line 26 of the first chamber 4 and in the feed line 27 of the second chamber 6 allow a volume flow of a substance entering at the inlet to be controlled. This substance can in particular be parahydrogen gas. A liquid 12 can also be fed into the first chamber 4 and a further liquid 13 into the second chamber 6 by means of the valves 40.

A further valve 43 is positioned between the first chamber 4 and the second chamber 6. When this valve 43 is closed, it is possible for example for the first chamber 4 to serve as an antechamber. For example, if there is water in the first chamber 4 and parahydrogen gas is fed in via the inlet 48, this allows a hydrogen solution 14 to be presaturated in the first chamber 4. If the second chamber 6 is filled with a further liquid 13 that contains a catalyst 22 and the tracer molecules 20 and if a higher pressure is set in the first chamber 4 than in the second chamber 6, opening the valve 43 then causes the hydrogen solution 14 to flow from the first chamber 4 into the second chamber 6, resulting in the mixing therein of the two liquids 12, 13 to form the reaction mixture 10. The mixing brings the tracer molecules 20 into contact with the hydrogen 16 from the hydrogen solution 14. The hydrogenation reaction initiated by mixing in turn results in the hydrogenation of the tracer molecules 20.

A substance may be discharged from the chambers 4 or 6 via the valve 41 positioned at the outlets 28 and 29. These valves 41 can likewise be used for pressure compensation or for pressure adjustment. A valve 45 not shown in more detail is also positioned on the line 36. Opening this valve 45 allows hydrogenated and/or hyperpolarized tracer molecules 20 to be fed to a further use via said line 36.

FIG. 5 shows an alternative embodiment of a device according to the invention for the hydrogenation of hyperpolarizable tracer molecules 20, 88 to 98 for magnetic resonance imaging. In contrast to the device 1 shown in FIG. 4, the reactor 2 in the alternative exemplary embodiment has only one first chamber 4. This chamber 4 has a feed line 26 and a further outlet line 36. A valve 40, 41 is positioned at each of these connections.

In addition, positioned on a transparent wall of the chamber 4 there is an emitter 46 capable of emitting into the chamber 4 electromagnetic waves of a defined wavelength, such as a defined color in the visible range or UV light having a wavelength that can have for example a value between 200 nm to 250 nm. If the chamber 4 is now filled with all the substances required for the hydrogenation reaction, so that the reaction mixture 10 is already present in the chamber 4, and if a light-switchable catalyst 22 is used, the catalyst 22 can be switched through activation of the emitter 46, thereby initiating the hydrogenation reaction. In an alternative exemplary embodiment, the wall is sound-permeable and the emitter 46 emits sound waves that activate a catalyst 22 responsive to this. In a further alternative exemplary embodiment, instead of a catalyst 22 activatable by irradiation, the tracer molecules 88 are brought to an excited electronic state by irradiation with electromagnetic radiation of a suitable wavelength, for example with UV light.

FIG. 6 shows a measuring device 52 prepared for an MR measurement in a patient 34, in which a device 1 as shown in FIG. 4 or FIG. 5 is positioned.

The measuring device 52 includes a cylinder 30 in which parahydrogen gas is stored. The parahydrogen gas can enter the reactor 2 via the valve 42 and the inlet 48. In addition, there are means with which the tracer molecules 20 and the catalyst 22 can also enter the reactor 2. The tracer molecules 20 can then be hydrogenated in the reactor 2 as described above. The reactor 2 is positioned in a measurement volume of an MR scanner 32. The MR scanner 32 serves at the same time as a polarizer for the hyperpolarization of the hydrogenated tracer molecules 20, which can be carried out as previously described above. The reactor 2 is then connected via the line 36 to an injection catheter, at the end of which is positioned a cannula 38 fitted to a patient 34. This allows the solution containing hyperpolarized tracer molecules 20 to be injected into the patient 34 as a contrast medium, thereby providing a contrast medium for the subsequent MR measurement.

In summary, in a method 100 to 192 in which hyperpolarizable tracer molecules 20, 88 to 98 are hydrogenated for magnetic resonance imaging and optionally then also hyperpolarized, it is proposed that a hydrogen solution 10, 12, 14 having a saturation factor of at least 50% is prepared in a first method step 104 and the hydrogenation reaction 186 to 190 initiated only in a subsequent second method step 106. The invention further comprises a device 1 with which the method 100 to 192 according to the invention can be executed.

LIST OF REFERENCE SYMBOLS

1 Device
2 Reactor
4 First chamber
6 Second chamber
10 Reaction mixture
12 Liquid
13 Further liquid
14 Hydrogen solution
16 Hydrogen
18 Hydrogen gas
20 Hyperpolarizable tracer molecule for MR imaging
22 Catalyst
24 First fill-volume
26 Feed line from 4
27 Feed line from 6
28 Outlet from 4
29 Outlet from 6
30 Cylinder
32 MR scanner
34 Patient
36 Line
37 Connecting line
38 Cannula
40 Valve
41 Further valve
42 Valve of 30
43 Valve of 37
44 Heating element
45 Valve of 36
46 Emitter
48 Inlet
50 Outlet
52 Measuring device
80 Complex
82 Further complex
83 Hydrogen gas
84 Norbornadiene
86 Catalyst
88 Unsaturated tracer molecule
90 Further complex
92 Further complex
94 Further complex
96 Hydrogenated tracer molecule
97 Excited tracer molecule
98 Hyperpolarized tracer molecule
99 UV light
100 Initialization
102 Supply of parahydrogen gas
104 Preparation of mixtures of substances
106 Mixing of mixtures of substances
108 Use of an SOT sequence
110 End of method
180 Exchange reaction
182 Cleavage reaction
184 Addition reaction
186 Addition reaction
188 Hydrogenation reaction
190 Cleavage reaction
192 Hyperpolarization through transfer of spin order
202 Preparation of a reaction mixture
204 Irradiation
206 Hydrogenation reaction
208 Hyperpolarization through transfer of spin order

The invention claimed is:

1. A method (100 to 206) in which hyperpolarizable tracer molecules (20, 88 to 98) are hydrogenated for magnetic resonance imaging, the method comprising:
bringing the tracer molecules (20, 88 to 98) into contact with hydrogen (14, 16, 18, 83) in a reaction mixture (10, 12, 14) and initiating a hydrogenation reaction in the reaction mixture (10, 12, 14), including
in a first method step (104, 202), dissolving the hydrogen (14, 16, 18, 83) in a liquid (10, 12, 14), resulting in the preparation of a hydrogen solution (10, 12, 14) having a saturation factor of at least 50%, and
in a subsequent second method step (106, 204) initiating the hydrogenation reaction (186 to 190, 206).

2. The method as claimed in claim 1, wherein the saturation factor is at least 80%.

3. The method as claimed in claim 1, further comprising preparing the reaction mixture (10, 12, 14) in the first method step (104, 202), wherein the reaction mixture is a homogeneous or heterogeneous mixture that contains all the substances involved in the hydrogenation reaction.

4. The method as claimed in claim 1, further comprising initiating the hydrogenation reaction (186 to 190, 206) by the hydrogen solution (12, 14) being mixed with a further reactant (20, 22, 86 to 98) or mixture of reactants (20, 22, 86 to 98) in the second method step (106, 204).

5. The method as claimed in claim 1, further comprising initiating the hydrogenation reaction (186 to 190, 206) by the reaction mixture (10, 12, 14) being irradiated (204) in the second method step (106, 204).

6. The method as claimed in claim 1, further comprising enriching the liquid (10, 12, 14) with a substance that increases an uptake capacity of the liquid (10, 12, 14) for hydrogen (14, 16, 18).

7. The method as claimed in claim 1, further comprising presaturating the liquid or a further liquid (13) that comes into contact with a catalyst (22, 86) with a hydrogen gas (18, 83).

8. The method as claimed in claim 7, further comprising in the first step, pressurizing the hydrogen gas (18, 83) to above atmospheric pressure, and carrying out the hydrogenation reaction (186 to 190, 206) under elevated pressure.

9. The method as claimed in claim 8, wherein the hydrogenation reaction (186 to 190, 206) taking place under elevated pressure is carried out below an actual boiling temperature and above a boiling temperature at atmospheric pressure.

10. The method as claimed in claim 8, wherein the elevated pressure is lower than the pressure of the hydrogen gas (18, 83).

11. The method as claimed in claim 1, further comprising, during or after the initiation of the hydrogenation reaction (186 to 190, 206), reducing a pressure in a chamber (4, 6) of a reactor (2) in which the hydrogenation reaction (186 to 190, 206) takes place, resulting in at least one of (a) an escape of hydrogen (14, 16, 18, 83) as a consequence of supersaturation, with attendant bubble formation, or (b) a boiling point of at least one of a substance (12, 13, 14) that is added to the reaction mixture (10, 12, 14) or a boiling point of the reaction mixture (10, 12, 14) being exceeded.

12. The method as claimed in claim 1, further comprising, after initiation of the hydrogenation reaction (186 to 190, 206), bringing the reaction mixture (10, 12, 14) into contact with a hydrogen gas (18, 83).

13. A method (100 to 208) in which tracer molecules (20, 88 to 98) for magnetic resonance imaging are hyperpolarized, comprising carrying out the method (100 to 206) as claimed in claim 1.

14. A device (1) for the hydrogenation of hyperpolarizable tracer molecules (20, 88 to 98) for magnetic resonance imaging, the device comprising: a reactor (2) for hydrogenating the tracer molecules (20, 88 to 98), the reactor (2) includes a first chamber (4) having a first fill-volume (24), which has at least one of a feed line (26) for hydrogen gas (18, 83) or a liquid (10, 12, 13, 14), and the device (1) is configured to carry out the method (100 to 206) as claimed in claim 1.

15. The method as claimed in claim 1, further comprising initiating the hydrogenation reaction (186 to 190, 206) by a switchable catalyst (22, 86) being activated in the second method step (106, 204).

16. The method as claimed in claim 1, further comprising, adding an H2 donor to the reaction mixture (10, 12, 14), and removing the H2 donor again after the hydrogenation reaction (186 to 190, 206).

17. The method as claimed in claim 1, further comprising preparing the reaction mixture (10, 12, 14) in the second method step (106, 204), and initiating the hydrogenation reaction (186 to 190, 206) directly by the preparation of the reaction mixture (10, 12, 14).

* * * * *